United States Patent
Paul et al.

(10) Patent No.: US 8,283,185 B2
(45) Date of Patent: Oct. 9, 2012

(54) MAGNETICALLY SUSCEPTIBLE PARTICLES AND APPARATUSES FOR MIXING THE SAME

(75) Inventors: Bentley Paul, Albuquerque, NM (US); Davenport Michael, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 485 days.

(21) Appl. No.: 12/447,060

(22) PCT Filed: Oct. 30, 2007

(86) PCT No.: PCT/US2007/083017
§ 371 (c)(1),
(2), (4) Date: Apr. 24, 2009

(87) PCT Pub. No.: WO2008/067103
PCT Pub. Date: Jun. 5, 2008

(65) Prior Publication Data
US 2010/0003167 A1    Jan. 7, 2010

Related U.S. Application Data

(60) Provisional application No. 60/855,268, filed on Oct. 30, 2006, provisional application No. 60/904,949, filed on Mar. 5, 2007.

(51) Int. Cl.
*G01N 33/553* (2006.01)
(52) U.S. Cl. ........ 436/526; 436/524; 436/525; 436/536; 436/149; 436/807; 436/810; 435/283.1; 435/287.1; 435/287.2; 435/287.3; 435/288.1
(58) Field of Classification Search .................. 436/526, 436/524, 525, 536, 149, 807, 810; 435/283.1, 435/287.1, 287.2, 287.3, 288.1
See application file for complete search history.

(56) References Cited

U.S. PATENT DOCUMENTS

| | | | |
|---|---|---|---|
| 3,440,731 A | 4/1969 | Tuthill | |
| 3,970,518 A | 7/1976 | Giaever | |
| 3,984,309 A * | 10/1976 | Allen et al. | 209/214 |

(Continued)

FOREIGN PATENT DOCUMENTS

JP    2005009905 A    1/2005

OTHER PUBLICATIONS

Baxendale et al; A flow process for the multi-step synthesis of the alkaloid natural product oxomaritidine: a new paradigm for molecular assembly; Chemical Communication; Feb. 15, 2005; pp. 2566-2568; worldwide.

(Continued)

*Primary Examiner* — Melanie J Yu
(74) *Attorney, Agent, or Firm* — Ellen M Gonzales; Gonzales Patent Services

(57) ABSTRACT

The present invention includes a magnetically susceptible polymer component, a method of making the same, and apparatuses and systems for mixing, separating or localizing a magnetically susceptible polymer compound in a reaction. The magnetically susceptible polymer component includes a polymer and a magnetically susceptible particle of a predetermined size, which yields a component having a much-improved magnetic reactivity due to the increase in magnetic material by mass percentage. The apparatuses and systems of the present invention employ controllable magnetic fields distributable in perpendicular directions in order to precisely control the orientation, position and relative motion of any magnetically susceptible components within a reaction vessel.

21 Claims, 6 Drawing Sheets

U.S. PATENT DOCUMENTS

| | | | |
|---|---|---|---|
| 3,985,649 | A | 10/1976 | Eddelman |
| 4,115,927 | A | 9/1978 | Rosensweig |
| 4,247,987 | A | 2/1981 | Coulaloglou et al. |
| 4,261,109 | A | 4/1981 | Mikus et al. |
| 4,283,204 | A | 8/1981 | Savage |
| 4,319,892 | A * | 3/1982 | Waghorne et al. ............... 95/27 |
| 4,335,094 | A | 6/1982 | Mosbach |
| RE31,439 | E | 11/1983 | Rosensweig |
| 4,554,088 | A | 11/1985 | Whitehead et al. |
| 4,695,392 | A | 9/1987 | Whitehead et al. |
| 4,695,393 | A | 9/1987 | Chagnon et al. |
| 4,895,650 | A | 1/1990 | Wang |
| 4,988,618 | A | 1/1991 | Li et al. |
| 5,167,812 | A | 12/1992 | Graves |
| 5,186,827 | A | 2/1993 | Liberti et al. |
| 5,331,589 | A * | 7/1994 | Gambino et al. ............. 369/126 |
| 5,445,970 | A | 8/1995 | Rohr |
| 5,541,072 | A | 7/1996 | Wang et al. |
| 5,628,407 | A | 5/1997 | Gilbert et al. |
| 5,681,478 | A | 10/1997 | Lea et al. |
| 5,763,472 | A * | 6/1998 | de Faire ....................... 514/395 |
| 5,793,199 | A * | 8/1998 | Kasahara et al. ............. 324/204 |
| 5,837,144 | A | 11/1998 | Bienhaus |
| 5,925,573 | A | 7/1999 | Colin et al. |
| 6,013,531 | A | 1/2000 | Wang et al. |
| 6,040,192 | A | 3/2000 | Tuunanen |
| 6,193,829 | B1 | 2/2001 | Acciai et al. |
| 6,316,235 | B1 | 11/2001 | Mosbach et al. |
| 6,331,277 | B2 | 12/2001 | Tajima |
| 6,500,343 | B2 | 12/2002 | Siddiqi |
| 6,764,859 | B1 | 7/2004 | Krenwel et al. |
| 6,884,357 | B2 | 4/2005 | Siddiqi |
| 6,980,001 | B2 * | 12/2005 | Paley et al. ................... 324/318 |
| 6,980,004 | B2 | 12/2005 | Barbk |
| 6,995,021 | B2 | 2/2006 | Laitinen et al. |
| 7,014,799 | B2 | 3/2006 | Wang et al. |
| 7,042,216 | B2 | 5/2006 | Barbk |
| 7,160,241 | B1 * | 1/2007 | Herbst ............................ 600/13 |
| 7,196,604 | B2 * | 3/2007 | Sills et al. .................... 335/306 |
| 7,198,747 | B2 | 4/2007 | Yang et al. |
| 7,202,667 | B2 | 4/2007 | Barbic |
| 7,351,592 | B2 | 4/2008 | Storek et al. |
| 2001/0002315 | A1 | 5/2001 | Schultz et al. |
| 2002/0001855 | A1 | 1/2002 | Prentiss et al. |
| 2002/0166760 | A1 | 11/2002 | Prentiss et al. |
| 2002/0166800 | A1 | 11/2002 | Prentiss et al. |
| 2003/0158474 | A1 | 8/2003 | Scherer et al. |
| 2004/0021073 | A1 | 2/2004 | Barbic et al. |
| 2004/0077105 | A1 * | 4/2004 | Wu et al. ...................... 436/524 |
| 2005/0275494 | A1 | 12/2005 | Gharib |
| 2006/0127278 | A1 | 6/2006 | Gast et al. |
| 2007/0227304 | A1 * | 10/2007 | Keller et al. ................... 75/362 |

OTHER PUBLICATIONS

Biswal et al; Micromixing with Linked Chains of Paramagnetic Particles; Analytical Chemistry; Nov. 1, 2004; pp. 6448-6465; vol. 76, No. 21; worldwide.

Lehmann et al; Droplet-based DNA purification in a Magnetic Lab-on-a-chip; Chem. Int., 2006, pp. 3062-3067; country unknown.

Pamme; Magnetism and Microfluidics; Lab Chip; Nov. 28, 2005; pp. 24-38; worldwide.

Barbic et al; Electromagnetic micromotor for microfluidics applications; 2001; Applied Physics Letters; pp. 1399-1401; worldwide.

France et al; Performing the Synthesis of a Complex Molecule on Sequentially Linked Columns: Toward the Development of a Synthesis Machine; Jun. 9, 2005; Organic Letters; pp. 3009-30012; worldwide.

* cited by examiner

MAGNETICALLY SUSCEPTIBLE PARTICLES AND APPARATUSES FOR MIXING THE SAME

CLAIM OF PRIORITY UNDER 35 U.S.C. §365 and 35 U.S.C. §119

The present application claims the benefit of the filing date of PCT application serial number PCT/US07/83017, filed on Oct. 30, 2007 and entitled "Magnetically Susceptible Particles and Apparatuses for Mixing the Same," which claims the benefit of the filing date of U.S. provisional patent application Ser. No. 60/855,268, filed on Oct. 30, 2006 and entitled "Magnetic Chemistry Stirred Directly by an Electromagnetic Reactor," and U.S. provisional patent application Ser. No. 60/904,949, filed on Mar. 5, 2007 and entitled "Apparatus and Method for the Stirring of Chemical Reactions."

BACKGROUND

1. Field of the Present Invention

The present invention relates generally to the fields of synthetic and analytical chemistry, and more specifically to chemical reactions with magnetically susceptible particles and apparatuses for their manipulation.

2. History of the Related Art

There has been a considerable growth in the use of magnetic particles to cause and/or regulate numerous biological reactions, including cell separation and expansion, protein and peptide sample fractionation, organelle isolation, capturing biotinylated targets, protein separation, RNA isolation, DNA purification, DNA differentiation, immunochemistry, pathogen detection, molecular imaging and drug delivery. The control and use of magnetic particles in reactions has also been the subject of keen interest of many chemists. Unfortunately, the states of the art in the development of new magnetic particles and devices for their optimal control both leave a great deal of room for improvement with respect to complexity, economy, efficiency, versatility and environmental impact.

As shown in FIG. 1, a typical magnetically susceptible polymer particle is formed through a chemical reaction between a polymer (X) and magnetite particle having hydroxyl attached thereto. The hydroxyl allows for a covalent bond between the polymer and the magnetite. In other applications, the polymer can be non-covalently associated as well as covalently bonded to a magnetic core. Many commercial variations of these types of products are available today, and are used with moderate success in the laboratory and industrial settings. To the extent that any components are devised without the use of covalent bonding with a single magnetic core, they are typically restricted to being no more than five percent magnetic material by mass, thus requiring very large magnetic fields with which to interact in a stirring or mixing apparatus.

Several devices have been described that propose to stir or otherwise cause the motion of magnetic particles. Unfortunately, each of these magnet configurations tends to result in sparse and/or weak magnetic fields. Moreover, to the extent that any of the magnets in existing devices are movable with respect to the reaction vessel, such movement only results in the movement of the sparse and/or weak magnetic field, which can further complicate the motion of the magnetic particles in the reaction vessel.

There is a need in the art for a more efficient and cost-effective magnetically susceptible polymer that includes a significant improvement in the magnetic mass as a percentage of weight and thus a higher magnetic reactivity. Additionally, there is a need in the art for new devices or apparatuses for mixing magnetically susceptible particles that employ denser, stronger and more predictable magnetic fields and have lower costs of operation and manufacture.

SUMMARY OF THE PRESENT INVENTION

Accordingly, the present invention includes magnetically susceptible polymer components and a method of making the same. The magnetically susceptible polymers include polymers formed through the polymerization of monomers or polymer precursors; and magnetically susceptible particles of an approximate diameter of less than one micrometer. The magnetically susceptible particles are sterically containable within the polymers such that the components are greater than five percent magnetically susceptible particles by mass. The method of preparing magnetically susceptible polymer components includes the steps of providing monomers adapted to polymerize in a solution; and introducing magnetically susceptible particles of an approximate diameter of less than one micrometer into the solution such that at least a portion of the magnetically susceptible particles are sterically constrained within at least a portion of the polymers such that the components are greater than five percent magnetically susceptible particles by mass.

The present invention further includes multiple apparatuses for manipulating a magnetically susceptible component, wherein the manipulation can include, but is not limited to, mixing a material with the magnetically susceptible component, separating the magnetically susceptible component from a non-magnetic or less-magnetic other particle, or localizing the magnetically susceptible component within a region of a reaction vessel. A first apparatus for mixing, separating or localizing a magnetically susceptible component includes a container for receiving a reaction vessel and defining a longitudinal axis as well as one or more segments of wiring arranged substantially parallel to the longitudinal axis. The first apparatus also includes an electrical source connected to the segment of wiring, such that in response to an electrical current passing from the electrical source to the segment of wiring, the electrical current generates a magnetic field substantially perpendicular to the longitudinal axis. The first apparatus can further include means for adjusting the relative position of the segment of wiring relative to the container along the longitudinal axis, thereby promoting the motion of any magnetically susceptible particles along the longitudinal axis.

The present invention further includes a second apparatus for mixing, separating or localizing a magnetically susceptible component. The second apparatus includes a cavity for mixing, separating or localizing the magnetically susceptible component with an additional substance and a first coil disposed substantially circumferentially about the container in a first position about a central axis of the cavity. The second apparatus also includes a second coil disposed substantially circumferentially about the container in a second position about the central axis. The second apparatus can further include a first electrical source connected to the first coil such that in response to a first electrical current passing from the electrical source through the first coil, the first electrical current generates a first magnetic field substantially parallel to the central axis as well as a second electrical source connected to the second coil such that in response to a second electrical current passing from the electrical source through the second coil, the second electrical current generates a second magnetic field substantially parallel to the central axis. The second apparatus can be configured according to a number of geometries described herein.

The present invention also includes a third apparatus for mixing, separating or localizing a magnetically susceptible component. The third apparatus includes a container for receiving a reaction vessel and defining a longitudinal axis and a first segment of wiring arranged substantially parallel to the longitudinal axis. The third apparatus also includes a second segment of wiring arranged in a substantially circumferential fashion about the longitudinal axis. An electrical source can be connected to the first segment of wiring and the second segment of wiring, such that in response to a first electrical current passing from the electrical source to the first segment of wiring, the first electrical current generates a first magnetic field substantially perpendicular to the longitudinal axis. Similarly, in response to a second electrical current passing from the electrical source to the second segment of wiring, the second electrical current generates a second magnetic field substantially parallel to the longitudinal axis. The magnetic fields can be used to cause the movement of one or more magnetically susceptible components in both the longitudinal and circumferential directions, giving a user complete control of the components in three-dimensions through selective activation or deactivation of the first and second segments of wiring.

Other features and advantages of the present invention are described in detail below with reference to the following Figures.

DETAILED DESCRIPTION OF THE PREFERRED EMBODIMENTS

The following description of the example embodiments is provided to enable any person skilled in the art to make or use the present invention. Various modifications to these embodiments will be readily apparent to those skilled in the art, and the generic principles defined herein may be applied to other embodiments without departing from the spirit or scope of the invention as set forth in the appended claims. As used herein, the term magnetically reactive denotes a property of a particle through which an external electromagnetic or magnetic field can induce motion of the particle and/or exert a force on the particle. The terms mix, separate, isolate and localize, used in any form herein, should be understood to denote specific examples of the various ways in which a magnetically susceptible particle can be manipulated by an external magnetic field, and such terms are not meant to be exclusive, but rather exemplary in nature.

Figure 1:
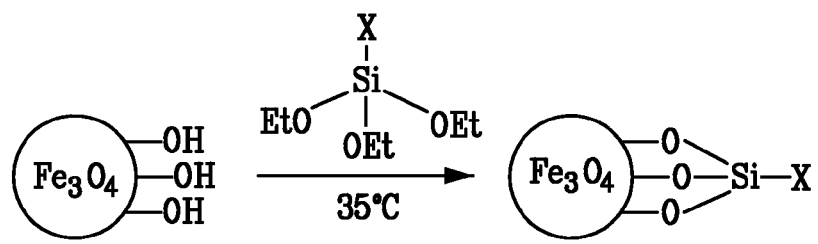
FIG. 1 is a schematic diagram of a magnetically susceptible polymer particle in accordance with the prior art.
Figure 2:
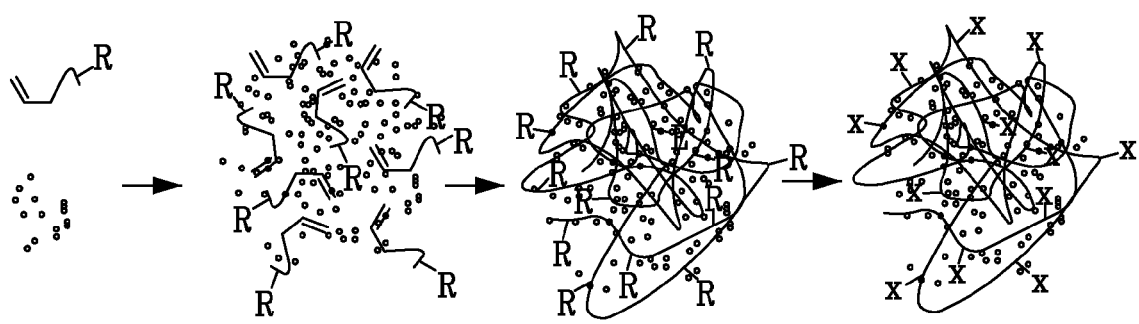
FIG. 2 is a schematic diagram of the formation of a magnetically susceptible polymer particle in accordance with one example embodiment of the present invention.

One aspect of the present invention includes magnetically susceptible polymer components composed of polymers formed through the polymerization of monomers or polymer precursors and magnetically susceptible particles of an approximate diameter of less than one micrometer. In one example embodiment, the magnetically susceptible particles are sterically containable within the polymers such that the components are greater than five percent magnetically susceptible particles by mass. As shown in FIG. 2, a group of polymer precursors (R) are combined with magnetically susceptible particles (designated by the dots). Through a polymerization reaction, the polymer precursors (that contain the functionality of generic R) form a polymer, within which the magnetic particles are contained sterically, as opposed to through a covalent bond. As the magnetic particles are sufficiently small in size, it is possible to sterically contain a large amount of magnetic material within the polymer, thereby resulting in a magnetically susceptible polymer component that is more highly magnetically reactive to any external electromagnetic fields.

In one variation of the example embodiment, the magnetically susceptible particles range in diameter between 10 nanometers and one micrometer. Suitable diameters of the magnetically susceptible particles can be in the range between twenty and fifty nanometers, within which the particles have shown a high degree of steric containment within the polymer. The magnetically susceptible particles can be any type of material that is reactive to a magnetic or electromagnetic field, including for example particles of iron oxide (II), iron oxide (III) and iron oxide (II, III), nickel, nickel oxide, samarium cobalt, or any other suitable inorganic or organic particle including manganese, lanthanide series elements such as neodymium and erbium, magnetic alloys such as aluminum, nickel, cobalt and copper alloys, metal oxides such as chromium dioxide, cobalt oxide, nickel oxide, or manganese oxide, composite materials such as ferrites or ceramic materials. Alternatively, the magnetically susceptible polymer components can be composed of on or more different types of magnetically susceptible particles, such as two or more of iron oxide (II), iron oxide (III) and iron oxide (II, III), nickel, nickel oxide, samarium cobalt, or any other suitable inorganic or organic particle including manganese, lanthanide series elements such as neodymium and erbium, magnetic alloys such as aluminum, nickel, cobalt and copper alloys, metal oxides such as chromium dioxide, cobalt oxide, nickel oxide, or manganese oxide, composite materials such as ferrites or ceramic materials.

In another variation of the example embodiment, the components are between five and forty-nine percent magnetically susceptible particles by mass. In some experiments conducted by the inventors, the components measured at approximately forty percent magnetically susceptible particles by mass. By selecting a magnetically susceptible particle of a suitably low size or diameter, the polymer can form itself around a much larger quantity of magnetic material and sterically contain the magnetic material. As such, the magnetically susceptible particles of this variation of the example embodiment are substantially more magnetically reactive than those currently used in the state of the art. Alternatively, the components can be designed to be approximately forty-nine percent magnetically susceptible particles by mass, yielding even more efficiency in any reaction in which the components may be used.

In another variation of the example embodiment, the polymers can be adapted to function in a predetermined fashion depending upon the reaction for which they are being used. For example, the polymers can be adapted to function a catalyst, a reagent, a substrate or a scavenger, or any suitable combination thereof, denoted (X) in FIG. 2. In another variation of the example embodiment, the polymers can be adapted to recognize a predetermined biological agent or chemical agent, such as for example predetermined characteristics for cell separation and expansion, predetermined proteins for protein and peptide sample fractionation, predetermined characteristics for organelle isolation, predetermined proteins for capturing biotinylated targets, predetermined proteins for performing protein separation, RNA molecules for performing RNA isolation, DNA molecules for performing DNA purification or differentiation, antigens or antibodies for use in immunochemistry, pathogens for pathogen detection, other predetermined molecules in molecular imaging and one or more pharmaceutical compounds for use in drug delivery.

Alternatively, the magnetically susceptible polymer components can be composed of two or more different types of polymers having different functionality. For example, the magnetically susceptible polymer components can be composed of two or more of a catalyst, a reagent, a substrate or a scavenger polymer. Components containing two more magnetic particles (of the same or differing types noted above) can be easier to conform and/or configure according to the specific functionality desired. In particular, in a magnetic field the molecule or component can exhibit unique and desirable intermolecular and intramolecular control as well as stereocontrol and regiocontrol within any number of reactions.

In another aspect, the present invention includes a method of preparing magnetically susceptible polymer components. The example method includes the steps of providing monomers or polymer precursors adapted to polymerize in or out of a solution and introducing magnetically susceptible particles of an approximate diameter of less than one micrometer into the solution such that at least a portion of the magnetically susceptible particles are sterically constrained within at least a portion of the polymers such that the components are greater than five percent magnetically susceptible particles by mass. As noted above, the magnetic particles are sufficiently small in size such that it is possible to sterically contain a large amount of magnetic material within the polymer, thereby resulting in a magnetically susceptible polymer component that is more highly reactive to any external electromagnetic fields.

In one variation of the example method, the magnetically susceptible particles range in diameter between 10 nanometers and one micrometer. Suitable diameters of the magnetically susceptible particles can be in the range between twenty and fifty nanometers, within which the particles have shown a high degree of steric containment within the polymer. The magnetically susceptible particles can be any type of material that is reactive to a magnetic or electromagnetic field, including for example particles of for example particles of iron oxide (II), iron oxide (III) and iron oxide (II, III), nickel, nickel oxide, samarium cobalt, or any other suitable inorganic or organic particle including manganese, lanthanide series elements such as neodymium and erbium, magnetic alloys such as aluminum, nickel, cobalt and copper alloys, metal oxides such as chromium dioxide, cobalt oxide, nickel oxide, or manganese oxide, composite materials such as ferrites or ceramic materials. Alternatively, the magnetically susceptible polymer components can be composed of two or more different types of magnetically susceptible particles, such as two or more for example particles of iron oxide (II), iron oxide (III) and iron oxide (II, III), nickel, nickel oxide, samarium cobalt, or any other suitable inorganic or organic particle including manganese, lanthanide series elements such as neodymium and erbium, magnetic alloys such as aluminum, nickel, cobalt and copper alloys, metal oxides such as chromium dioxide, cobalt oxide, nickel oxide, or manganese oxide, composite materials such as ferrites or ceramic materials.

In another variation of the example method, the components are between five and forty-nine percent magnetically susceptible particles by mass. In some samples prepared by the inventors according to the methodology described herein, the components measured at approximately forty percent magnetically susceptible particles by mass. Selection of a magnetically susceptible particle of a suitably low size or diameter ensures that the polymer can receive a much larger quantity of magnetic material therein and sterically contain the magnetic material. As such, the magnetically susceptible particles of this variation of the example method are substantially more magnetically reactive than those currently prepared in the state of the art. Alternatively, the components can be designed to be approximately forty-nine percent magnetically susceptible particles by mass, yielding even more efficiency in any reaction in which the components may be used.

In another variation of the example method, the polymers can be adapted to function in a predetermined fashion depending upon the reaction for which they are being used. For example, the polymers can be adapted to function a catalyst, a reagent, a substrate or a scavenger, or any suitable combination thereof. In another variation of the example method, the polymers can be adapted to recognize a predetermined biological agent or chemical agent, such as for example predetermined characteristics for cell separation and expansion, predetermined proteins for protein and peptide sample fractionation, predetermined characteristics for organelle isolation, predetermined proteins for capturing biotinylated targets, predetermined proteins for performing protein separation, RNA molecules for performing RNA isolation, DNA molecules for performing DNA purification or differentiation, antigens or antibodies for use in immunochemistry, pathogens for pathogen detection, other predetermined molecules in molecular imaging and one or more pharmaceutical compounds for use in drug delivery.

Alternatively, the magnetically susceptible polymer components can be composed of two or more different types of polymers having different functionality. For example, the magnetically susceptible polymer components can be composed of two or more of a catalyst, a reagent, a substrate or a scavenger polymer. As noted herein, components containing two more magnetic particles (of the same or differing types noted above) can be easier to conform and/or configure according to the specific functionality desired. In particular, in a magnetic field the molecule or component can exhibit unique and desirable intermolecular and intramolecular control as well as stereocontrol and regiocontrol within any number of reactions.

Figure 3:
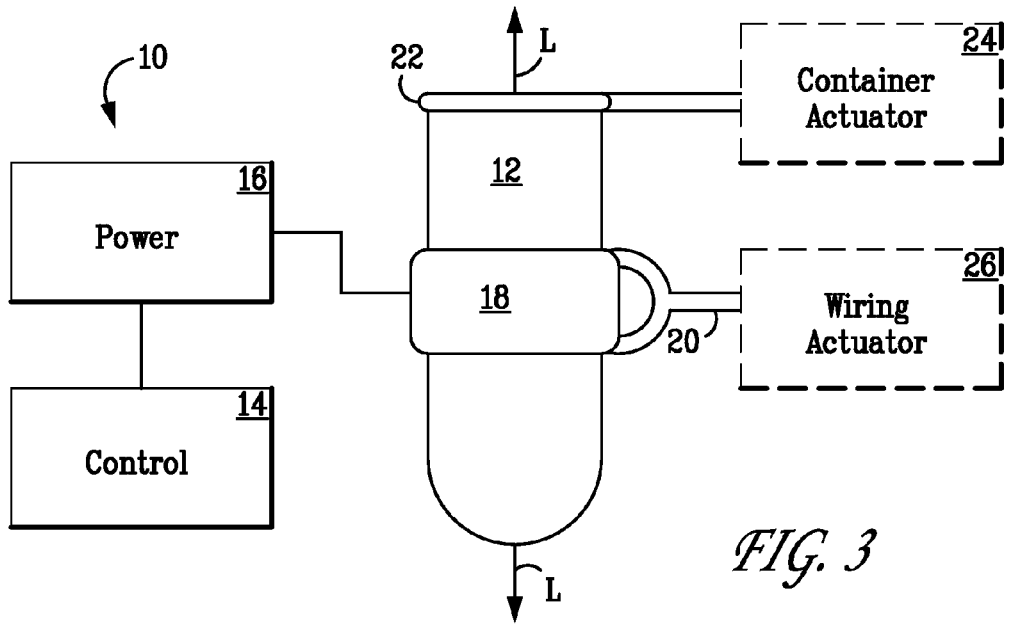
FIG. 3 is a schematic diagram of an apparatus for mixing, separating or localizing a magnetically susceptible particle with another substance in accordance with another example embodiment of the present invention.

The present invention further includes an apparatus for mixing, separating or localizing a magnetically susceptible component within a solution. One example embodiment of the apparatus of the present invention is shown in FIG. 3. As shown, the example apparatus 10 includes a container 12 for receiving a reaction vessel (not shown), which in turn can be used to hold and/or contain a solution and magnetically susceptible components for mixing, separating or localizing. The container 12 defines a longitudinal axis L, which can be oriented in any suitable fashion relative to any prevailing magnetic, electromagnetic or gravitational field for inducing the appropriate mixing, separating or localizing results. For example, the container 12 can be oriented substantially vertically, substantially horizontally, at a predetermined constant angle or at a variable angle.

The example apparatus 10 can further include a segment of wiring 18 arranged substantially parallel to the longitudinal axis L. As shown in FIG. 3, the segment of wiring 18 forms a band or ring about the longitudinal axis L, within which individual wires are oriented substantially parallel to the longitudinal axis L such that any magnetic field generated by the segment of wiring 18 is substantially circumferentially perpendicular to the longitudinal axis L (e.g., along the direction of the variable θ in a cylindrical coordinate system). For example, the segment of wiring 18 can be composed of a motor-type wiring, in which wires are wrapped substantially parallel to the longitudinal axis L and forming a substantially uniform ring or band about the longitudinal axis L for inducing a circumferential magnetic field about the longitudinal axis L. The segment of wiring 18 can be connected directly to the container 12, or it can be arranged radially distally from the container 12, depending upon the characteristic magnetic field that a user is attempting to generate within the container 12. Alternatively, the position of the segment of wiring 18 can be radially varied relative to the container 12.

The segment of wiring 18 can comprise two or more discrete wires that can be connected to an electrical source 16 in series or in parallel, allowing for both synchronous or asynchronous magnetic field generation by the individual wires. For example, the discrete wires can receive current independently from one another, allowing for sequential or staggered generation of magnetic fields within the container 12. Wiring 18 can include for example a motor-type orientation of conductive wiring adapted to produce a circumferential magnetic field about the longitudinal axis L. Alternatively, the segment of wiring 18 can be wrapped around a non-permanent magnetic material, that can include for example a motor wire stator-type relationship such that all of the portions of the segment of wiring 18 nearest the container 12 are substantially uniformly directed.

The example apparatus 10 can further include the electrical source 16 connected to the segment of wiring 18. The electrical source 16 functions to provide electrical current to the segment of wiring 18 according to one or more predetermined current characteristics. As noted above, in response to an electrical current passing from the electrical source 16 to the segment of wiring 18, the electrical current generates a magnetic field substantially perpendicular to the longitudinal axis L, which in operation can cause a magnetic force on any magnetic material within the container 12. The example apparatus 10 can further include means for adjusting the relative position of the segment of wiring relative to the container along the longitudinal axis.

In one variation of the example apparatus 10, the means for adjusting can include an actuator 24 (shown in phantom) connected to the container 12 via a connector 22. The actuator 24 can be adapted to translate the container along the longitudinal axis L relative to the segment of wiring 18. Alternatively, the means for adjusting can include an actuator 26 (shown in phantom) connected to the segment of wiring 18 via a connector 20. The actuator 26 can be adapted to translate the segment of wiring 18 along the longitudinal axis L relative to the container 18. Each of the actuators 24, 26 function to adjust the relative longitudinal position of the container 12 and the segment of wiring 18 along the longitudinal axis L, thereby adjusting the longitudinal position of the magnetic field that can be generated by the segment of wiring 18 within the container 12. Each of the actuators 24, 26 can be any suitable mechanical or electromechanical device that is adapted to move an object a predetermined distance along a predetermined trajectory. Each of the actuators 24, 26 can be controlled manually or automatically, or any suitable combination thereof to generate the desired reaction results.

In another variation of the example apparatus 10, the apparatus 10 can include a temperature control means (not shown) connected to or disposed on one or both of the segment of wiring 18 and the container 12. The temperature control means functions to maintain a suitable reaction temperature while electrical current passes through the segment of wiring 18. For the segment of wiring 18, the temperature control means can include an internal or external core and/or wrap that insulates the container 12 from any heat generated by the segment of wiring 18 when it is conducting electricity. Alternatively, the temperature control means for the segment of wiring 18 can include both heating and cooling materials, such as a heat source and a heat sink, that are adjustable to maintain a specified temperature. The container 12 temperature control means can include for example a fluid bath within which the container 12 is submersible, a cooling or heating jacket disposable about the container 12, a cooling or heat exchanging apparatus operable as a heat sink or a heat source, or any other suitable means or mechanism for removing heat caused by the segment of wiring 18 away from the reaction within the container 12. In one alternative to the example apparatus 10, the temperature control means for both the segment of wiring 18 and the container 12 are adapted to maintain a substantially uniform temperature so as to optimize reaction conditions within the container 12 and prevent damage to wiring 18 while allowing wiring 118 to produce an optimal magnetic field.

In another variation of the example apparatus 10, the apparatus 10 can include a controller 14 connected to the electrical source 16. The controller 14 can be adapted to control one or more of a plurality of current parameters of the electrical source 16, such as for example a current magnitude, a current frequency, a current timing, and a current direction. In doing so, the controller 14 can be adapted to indirectly control the magnitude, frequency, timing and direction of any magnetic or electromagnetic field generated by the segment of wiring 18, thereby indirectly controlling various attributes of the reaction within the container 12.

The controller 14 can also be connected to one or more of the actuators 24, 26 for controlling the actuated movement of the container 12 relative to the segment of wiring 18. The controller 14 can be any suitable processor, microprocessor, computer, ASIC, integrated circuit, or device that is adapted to produce a predetermined output in response to a set of machine-readable or manual instructions. The controller 14 can be integrated within one of the electrical source 16 or actuators 24, 26, distributed among one or more of the electrical source 16 or actuators 24, 26, or operated as a stand-along modular component of the example apparatus 10.

Figure 4:
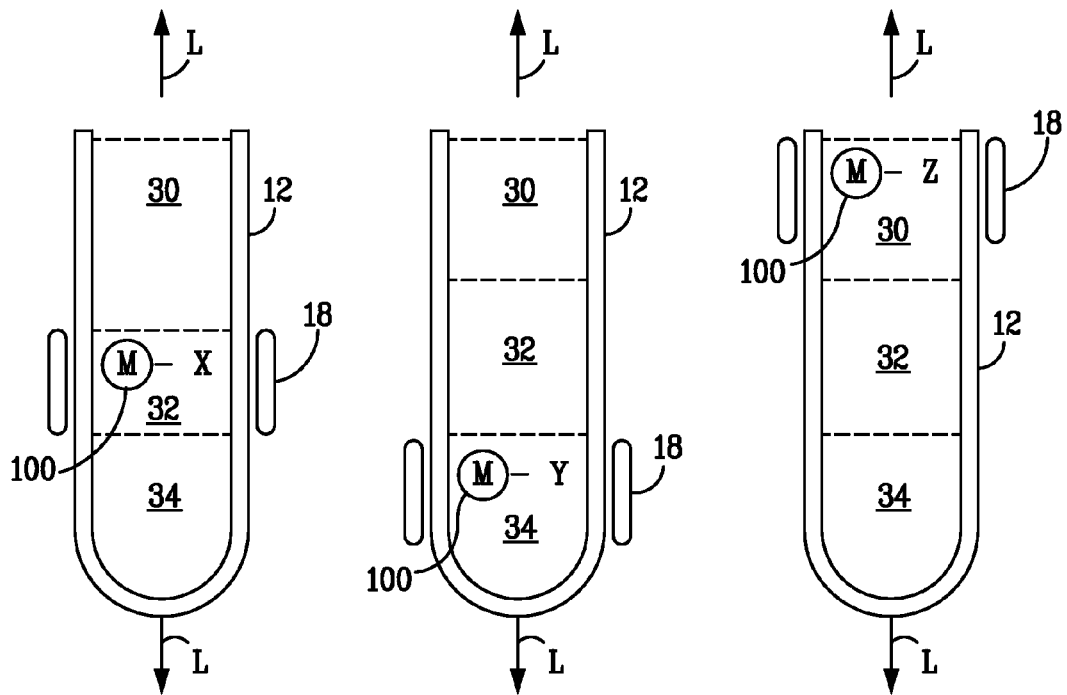
FIG. 4 is a schematic diagram of the apparatus of FIG. 3 in use according to one application of the example embodiment.

FIG. 4 is a schematic diagram of the example apparatus 10 in use according to one suitable application of the example apparatus 10. As shown in FIG. 4, more than one reaction can occur within the container simultaneously, and one or more of the magnetically susceptible polymer components 100 (M in reaction X, M in reaction Y, or M in reaction Z) can be activated within each distinct reaction by the positioning of the segment of wiring 18 relative to the container 12 along the longitudinal axis L. For example, the container 12 can have an organophilic reaction 30, a fluorophilic reaction 32 and an aqueophilic reaction occurring substantially simultaneously. The reactions 30, 32, 34 can be have their reaction rates increased by the mixing, separating or localizing of one or more of the magnetically susceptible polymer components 100 within the distinct regions. The magnetically susceptible polymer components 100 can be moved between the reactions 30, 32, 34 by causing the relative movement of the segment of wiring 18 relative to the container 12 along the longitudinal axis L. As noted above, the segment of wiring 18 can be configured such that, in response to electrical current passing there through, it generates a magnetic field that is substantially circumferentially perpendicular to the longitudinal axis L. The magnetic field in turn causes the magnetically susceptible components 100 to move in a substantially circumferential or spiral path about the longitudinal axis L, thereby stirring the reaction 30, 32, 34 in a predetermined manner.

Figure 5:
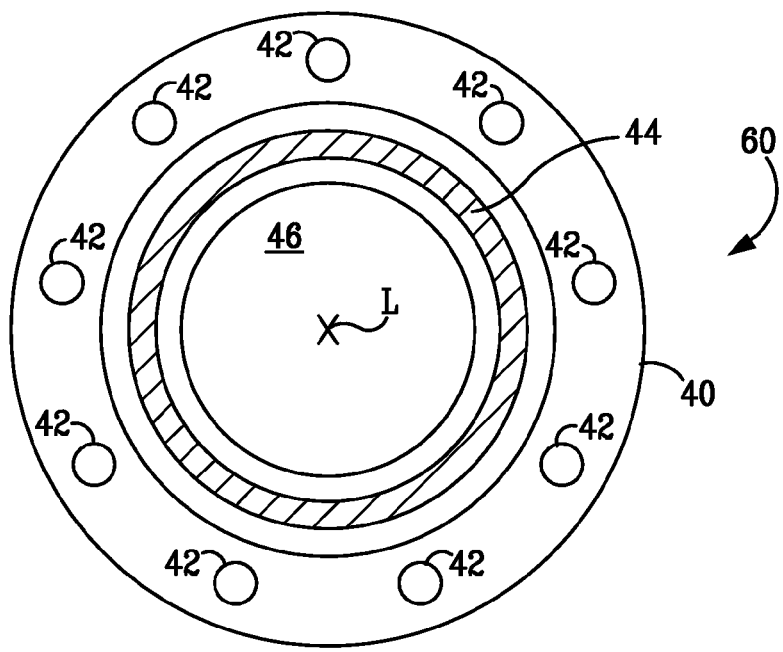
FIG. 5 is a cross-sectional view along a longitudinal axis of an apparatus for mixing a magnetically susceptible particle with another substance in accordance with another example embodiment of the present invention.
Figure 6:
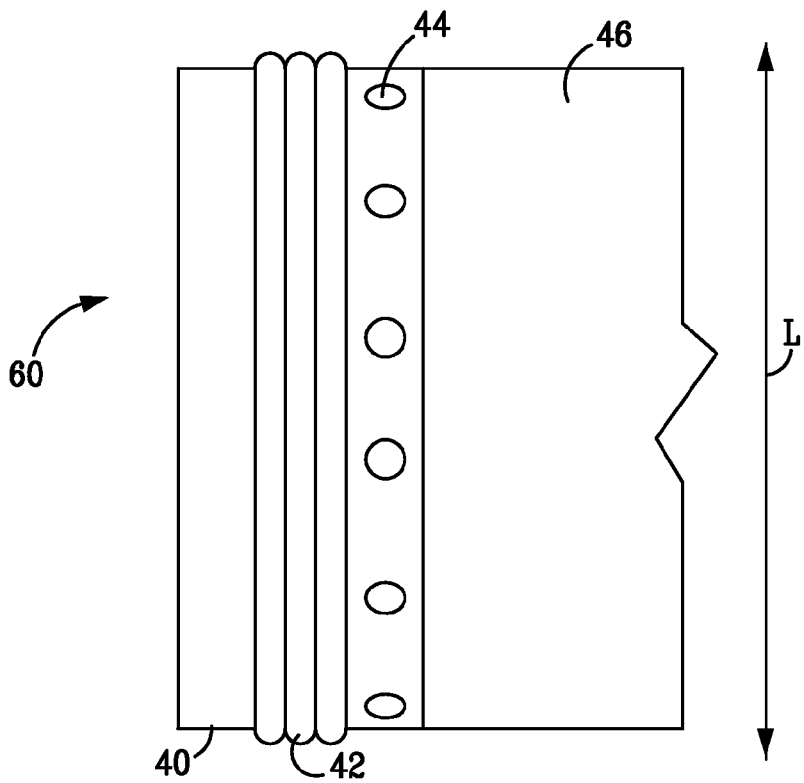
FIG. 6 is a cross-sectional view perpendicular to the longitudinal axis of the apparatus shown in FIG. 5.

The present invention further includes a second apparatus for mixing, separating or localizing a magnetically susceptible component. As shown in FIGS. 5 and 6, the example apparatus 60 includes a container 46 for receiving a reaction vessel and defining a longitudinal axis L. The example apparatus 60 further includes a first segment 42 of wiring arranged substantially parallel to the longitudinal axis L and a second segment of wiring 44 arranged in a substantially circumferential fashion about the longitudinal axis L. The example apparatus 60 can further include an electrical source (not shown) connected to the first segment of wiring 42 and the second segment of wiring 44. The first segment of wiring 42 is arranged such that in response to a first electrical current passing from the electrical source to the first segment of wiring 42, the first electrical current generates a first magnetic field substantially circumferentially perpendicular to the longitudinal axis L. The first segment of wiring 42 can include for example a motor-type orientation of conductive wiring adapted to produce a circumferential magnetic field about the longitudinal axis L. Similarly, the second segment of wiring 44 is arranged such that in response to a second electrical current passing from the electrical source to the second segment of wiring 44, the second electrical current generates a second magnetic field substantially parallel to the longitudinal axis L. The second segment of wiring 44 can include for example a conductive wire arranged in a substantially cylindrical fashion and adapted to produce a longitudinal magnetic field along the longitudinal axis L.

In operation, the first segment of wiring 42 functions to create a substantially circumferential magnetic field, which can be used as described above for stirring a magnetically susceptible particle substantially about the longitudinal axis L, thereby promoting a reaction within the reaction vessel. The second segment of wiring 44 functions to create a magnetic field that is substantially parallel to the longitudinal axis, which can be used for moving one or more magnetically susceptible particles along the longitudinal axis L. Accordingly, the simultaneous or systematic operation of the first and second segments of wiring 42, 44 can effectively cause the stirring of one or more magnetically susceptible particles at substantially any region within the container 46, giving a user complete three-dimensional control over the position and/or trajectory of the magnetically susceptible particles and thereby optimizing any reaction occurring therein. Alternatively, the first and second segments of wiring 42, 44 can each be composed of individual wires that can be individually controlled to provide variable, sequential, graded or otherwise custom generation of the resultant magnetic fields. A non-permanent magnetic material can be inserted between the first and second segments of wiring 42, 44, as well as between both the first and second segments of wiring 42, 44 and the container 46.

In one variation of the example apparatus 60, the example apparatus 60 includes a temperature control means (not shown) connected to or disposed on one, two are all of the container 46, the first segment of wiring 42 and the second segment of wiring 44. The temperature control means functions to maintain a suitable reaction temperature while electrical current passes through the first and second segments of wiring 42, 44. For the segments of wiring 42, 44, the temperature control means can include an internal or external core and/or wrap that insulates the container 46 from any heat generated by the segments of wiring 42, 44 when one or both are conducting electricity. Alternatively, the temperature control means for the segments of wiring 42, 44 can include both heating and cooling materials, such as a heat source and a heat sink, that are adjustable to maintain a specified temperature. The container 46 temperature control means can include for example a fluid bath within which the container 46 is submersible, a cooling or heating jacket disposable about the container 46, a cooling or heat exchanging apparatus operable as a heat sink or a heat source, or any other suitable means or mechanism for removing heat caused by the segment of wiring 42, 44 away from the reaction within the container 46. In one alternative to the example apparatus 60, the temperature control means for both the segments of wiring 42, 44 and the container 46 are adapted to maintain a substantially uniform temperature so as to optimize reaction conditions within the container 46 and prevent damage to wiring 42 and 44, while allowing wiring 42 and 44 to produce an optimal magnetic field.

In another variation of the example apparatus 60, the electrical source is adapted to provide electrical current to the first segment of wiring 42 and the second segment of wiring 44 in a substantially simultaneous fashion. In doing so, the electrical source can induce both longitudinal and circumferential magnetic fields within the container 46, thus causing both longitudinal and circumferential stirring motions of one or more magnetically susceptible particles. Alternatively, the electrical source can be adapted to provide electrical current to the first segment of wiring 42 and the second segment of wiring 44 in a substantially sequential fashion. By way of comparison, sequential powering of the first and second segments of wiring 42, 44 can cause an alternating, sequenced or ratioed presence of longitudinal and circumferential magnetic fields within the container 46. For example, the electrical source can be adapted to intersperse activation of the first segment of wiring 42 within a continuous activation of the second segment of wiring 44 in order to counter the effects of gravity, i.e., to raise any magnetically susceptible particles within the container 46 as they are falling under the influence of gravity.

In another variation of the example apparatus 60, the example apparatus 60 can include a controller (not shown) connected to the electrical source. As described above, the controller can be adapted to control one or more of a plurality of current parameters of the electrical source, including for example a current magnitude, a current frequency, a current timing, and a current direction. In doing so, the controller can be adapted to indirectly control the magnitude, frequency, timing and direction of any magnetic or electromagnetic field generated by the first and second segments of wiring 42, 44, thereby indirectly controlling various attributes of the reaction within the container 46. The controller can be any suitable processor, microprocessor, computer, ASIC, integrated circuit, or device that is adapted to produce a predetermined output in response to a set of machine-readable or manual instructions. The controller can be integrated within the electrical source or operated as a stand-along modular component of the example apparatus 60.

In another variation of the example apparatus 60, the example apparatus 60 can include another electrical source, such that each of the first and second segments of wiring 42, 44 are independently powered by a unique electrical source. Similarly, the controller noted above can be connected to each of the independent electrical sources and adapted to control one more of the aforementioned current parameters for each of the power sources.

The present invention further includes another apparatus for mixing, separating or localizing a magnetically susceptible component. The third example apparatus includes a cavity for mixing, separating or localizing the magnetically susceptible component with an additional substance and defining a central axis. The example apparatus further includes a first coil disposed circumferentially about the container in a first position about the central axis and a second coil disposed circumferentially about the container in a second position about the central axis. The example apparatus also includes a first electrical source connected to the first coil such that in response to a first electrical current passing from the electrical source through the first coil, the first electrical current generates a first magnetic field substantially parallel to the central axis; and a second electrical source connected to the second coil such that in response to a second electrical current passing from the electrical source through the second coil, the second electrical current generates a second magnetic field substantially parallel to the central axis. In a variation of the example apparatus, the first and second coils can be connected to a unitary, third electrical source having a switch, controller, or processor adapted to selectively provide electrical current to at least one of the first and second coils through the first and second electrical sources. The third example apparatus can be configured in numerous ways for generating specific types of reactions and reaction conditions within the cavity.

Figure 10:
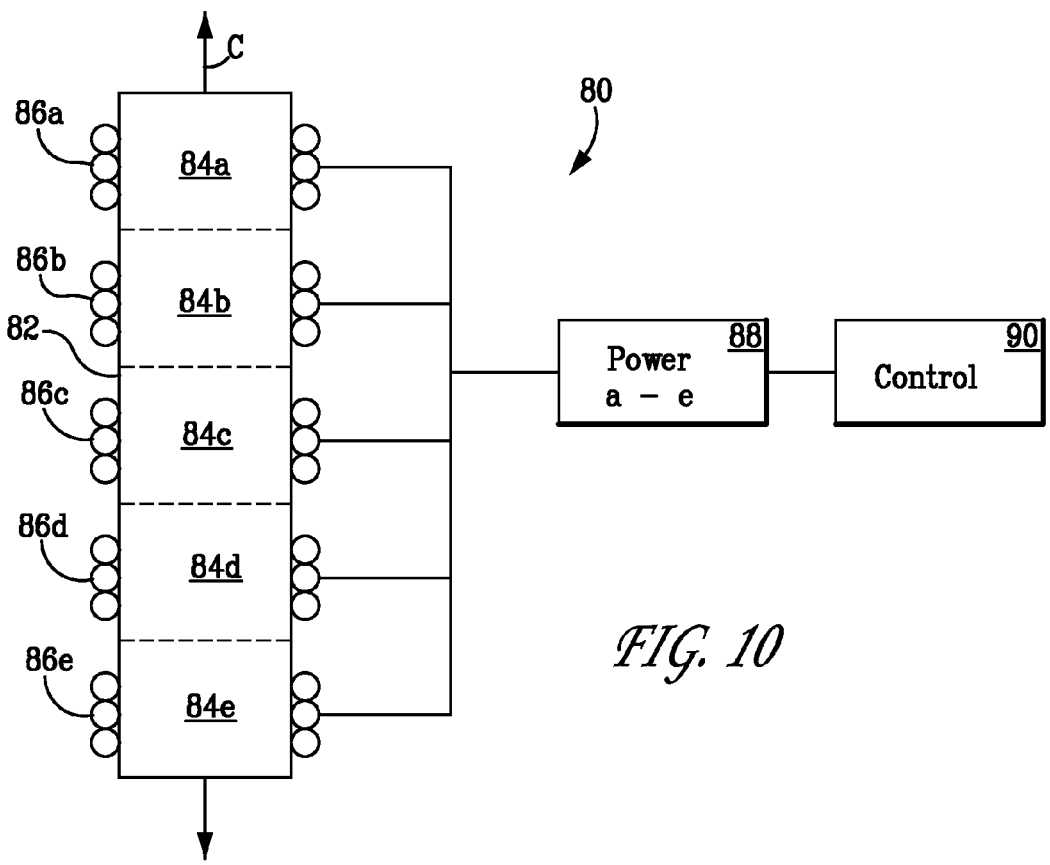
FIG. 10 is a schematic diagram of an apparatus for mixing a magnetically susceptible particle with another substance in accordance with another example embodiment of the present invention.

For example, FIG. 10 is a schematic illustration of one example embodiment of the aforementioned apparatus. As shown therein, the cavity of the example apparatus 80 defines a substantially cylindrical volume having a central axis C, about which a series of coils 86a, 86b, 86c, 86d, 86e are substantially circumferentially disposed. The example embodiment can also include a reaction vessel (not shown) disposable within the cavity. The reaction vessel can be of any suitable shape or size for conducting the desired reaction, for example ranging in size between a microcapillary tube to a beaker, vat or drum. The example embodiment can further include an isolating material, such as a copper strip, for substantially focusing a magnetic field generated by coil 86a into corresponding region 84a.

The example embodiment can also include an electrical source 88 adapted to power, in parallel or in series, each of the series of coils 86a, 86b, 86c, 86d, 86e. Each of the coils 86a, 86b, 86c, 86d, 86e are configured for generating a magnetic field substantially within a corresponding region 84a, 84b, 84c, 84d, 84e of the cavity. Each of the series of coils 86a, 86b, 86c, 86d, 86e can be alternatively be connected to one or more independent power sources, which can be distributed within the integrated electrical source 88 shown in FIG. 10. The example embodiment can further include a controller 90 adapted to control one or more of a plurality of current parameters of the electrical source 88, such as for example a current magnitude, a current frequency, a current timing, and a current direction. In an alternative embodiment, the controller 90 can be connected to more than one electrical source and adapted to control one or more of a plurality of current parameters for each electrical source to which it is connected.

The liquid can be introduced to the reaction under pressure from gravity or a pump to the vessel at region 84a and be permitted to leave the reaction vessel at region 84e, whilst the magnetic particles may be retained and manipulated by mixing separating or localization within the reaction vessel. Multiple reaction vessels (linked in series or parallel to allow liquid flow between the reaction vessels) placed in multiple electromagnetic devices would permit a series of simultaneous reactions.

The reaction vessel in region 84e can have a faucet to control liquid to leave the reaction vessel under gravity or pressure from gas or additional liquid (introduced to the reaction vessel at region 84a), whilst the magnetic particles may be retained and manipulated by mixing separating or localization within the reaction vessel.

Figure 11:
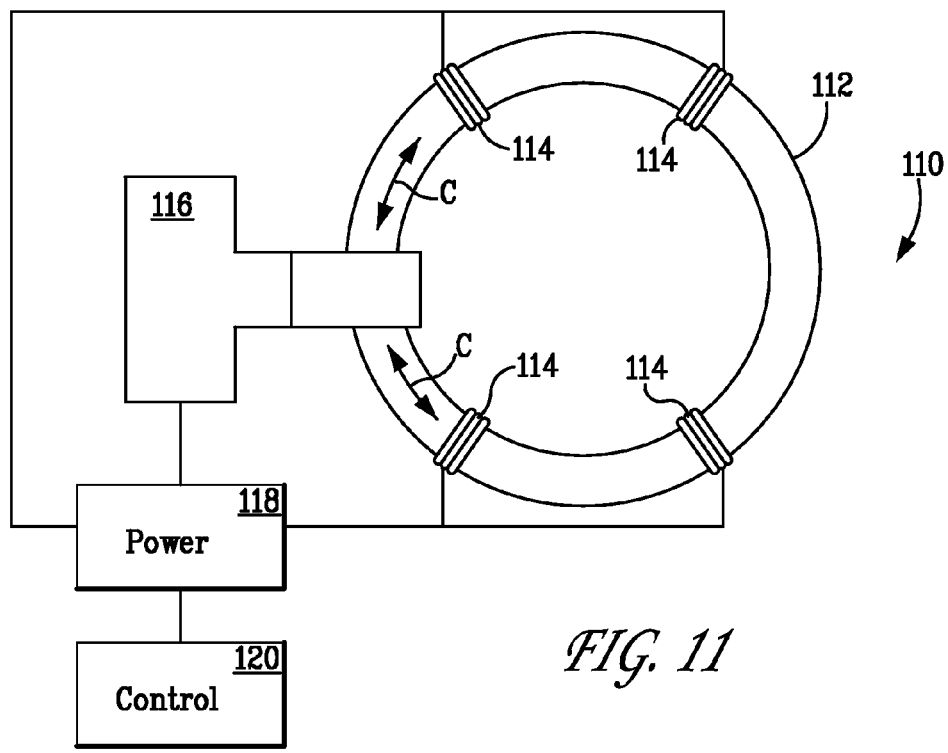
FIG. 11 is a schematic diagram of an apparatus for mixing a magnetically susceptible particle with another substance in accordance with another example embodiment of the present invention.

FIG. 11 schematically depicts another configuration for the third example apparatus of the present invention in which the cavity 112 defines a substantially toroidal volume that is well suited for causing reactions within a flow system. The example apparatus 110 can include one or more coils 114 disposed circumferentially about the central axis C of the cavity 112. As shown in FIG. 11, four coils 114 are disposed in quadrants surrounding the cavity 112, although any suitable number of coils 114 can be used with the example apparatus. As in the prior example embodiments, the coils 114 can be activated by an electrical source 118, which can be configured as a single unitary electrical source 118 connected to more than one of the coils 114, or as multiple independent electrical sources each connected to a single one of the coils 114.

The example apparatus 110 can further include a pump 116 connected to the cavity that is adapted to cause a material to flow within the cavity. For example, the material can include a solution of desired reactants as well as magnetically susceptible components adapted for stirring the reaction in accordance with the inventive principles described herein. The example apparatus 110 can further include one or more valves (not shown) connected to the cavity that are adapted to control the flow of the material within the cavity. The valves can be connected to an external control apparatus, such as a controller 120, for selectively actuating the valves at predetermined times within the course of the reaction. The valves (not shown) and/or coils 114 can be used for separating the magnetically susceptible particles and/or any other solid materials from the liquid, thereby allowing the liquid to flow through the pump 116 without fouling the pump with any solid materials and avoiding any damage to the magnetically susceptible particles.

Prior fluidized bed reactors tend to maintain the magnetic solid approximately stationary in an area of the flow channel. Any localized beneficial agitatory movement of the magnetic solid against the liquid flow ultimately will position the magnetic chemical at the end of the external magnetic field and the material must be moved back in the opposite (inferior agitatory) direction (the same direction as the liquid). The movement of magnetic solid outside the external magnetic field is passively in the direction of the liquid flow. Fortunately, the example apparatus 110 described herein allows a user to control movement of the magnetically susceptible component and the fluid in all directions (e.g. the magnetically susceptible can be moved anticlockwise and the pump can cause the liquid to move clockwise), which would tend to produce optimal mixing, separation or localization for the flow apparatus.

In another variation of the example embodiment, the apparatus 80, 110 can include a temperature control means (not shown) disposed or connected to one or both of the cavity 112 and the coils 114. As noted above, the temperature control means functions to maintain a suitable reaction temperature while electrical current passes through the coils 114 and protect coils 114 from damage while allowing coils 114 to produce an optimal magnetic field. For the coils 114, the temperature control means can include an internal or external core and/or wrap that insulates the cavity 112 from any heat generated by the coils 114 when one or more of the coils 114 are conducting electricity. Alternatively, the temperature control means for the coils 114 can include both heating and cooling materials, such as a heat source and a heat sink, that are adjustable to maintain a specified temperature. For the cavity 112, the temperature control means can include for example a fluid bath within which the cavity 112 is submersible, a cooling or heating jacket disposed around the cavity 112, a cooling or heat exchanging apparatus operable as a heat sink, or any other suitable means or mechanism for removing heat caused by the coils 114 away from the reaction within the cavity and/or reaction vessel.

In another variation of the example apparatus 80, 110, the example apparatus can include a controller 90, 120 adapted to control one or more of a plurality of current parameters of the first and second electrical sources 88, 118, such as for example a current magnitude, a current frequency, a current timing, and a current direction. As in prior example embodiments, the controller 90, 120 can be any suitable processor, microprocessor, computer, ASIC, integrated circuit, or device that is adapted to produce a predetermined output in response to a set of machine-readable or manual instructions. The controller 90, 120 can be integrated within one of the electrical source 88, 118, distributed between one and more of the electrical sources 88, 118, or operated as a stand-along modular component of the example apparatus 80, 110. The controller 90, 120 can be further adapted to control the electrical source 88, 118 to provide electrical current to the first and second coils in a predetermined pattern in order to optimize the mixing, separating or localizing within the apparatus 80, 110. The predetermined pattern can include for the provision of electrical current substantially simultaneously or providing current substantially sequentially.

Figure 12A:
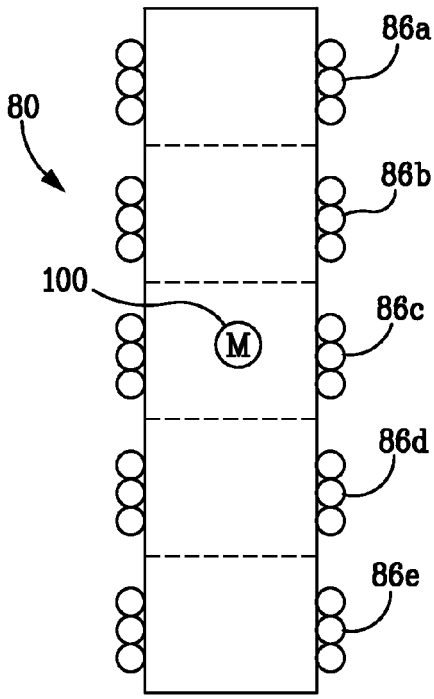
FIG. 12A is a schematic diagram of one application of the apparatus shown in FIG. 10.

For example, FIGS. 12A, 12B, 12C and 12D are illustrative of one application of the example apparatus 80 described above. In FIG. 12A, coil 86d can be activated with current running in a first direction that causes a magnetic field to move a magnetically susceptible component 100 towards coil 86b. Simultaneously or sequentially, coil 86b can be activated with current running in a second direction opposite the first direction that causes a magnetic field to move the magnetically susceptible particle 100 in the opposite direction towards coil 86d. As a result, synchronous or sequential activation of coils 86b, 86d will cause opposing magnetic fields to constrain the magnetically susceptible component 100 in the region near coil 86c. Oscillation of the respective magnetic fields generated by coils 86b, 86d will also cause the magnetically susceptible component 100 to oscillate, thus causing a substantially vertical, radial and/or circumferential stirring motion within the cavity. Activation of coil 86c will cause the magnetically susceptible component 100 to move to the region 84c directly adjacent to the coil 86c.

Figure 12B:
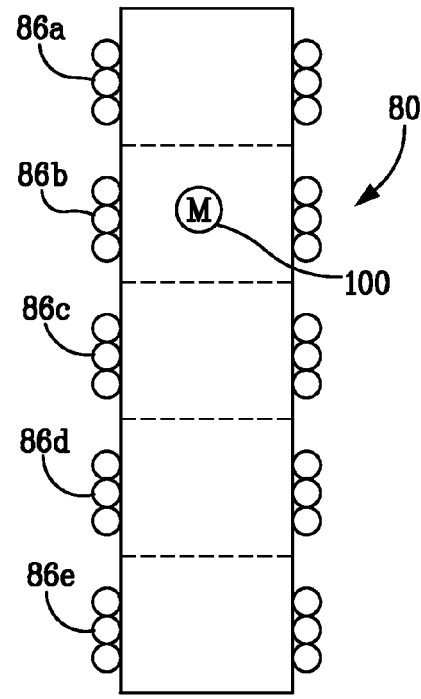
FIG. 12B is a schematic diagram of one application of the apparatus shown in FIG. 10.

Alternatively, FIG. 12B shows that simultaneous activation of at least coil 86b, and possibly coils 86c, 86d, 86e in a uniform direction will cause magnetically susceptible component 100 to be suspended in the region adjacent to coil 86b. This program of coil activation can be used, for example, to move any magnetic material to an opening of the cavity from where it can be removed following the reaction. That is, at the conclusion of a reaction, the example apparatus 80 can be used to move substantially all of the magnetic material in the direction desired by a user in order to remove the magnetic material.

Figure 12C:
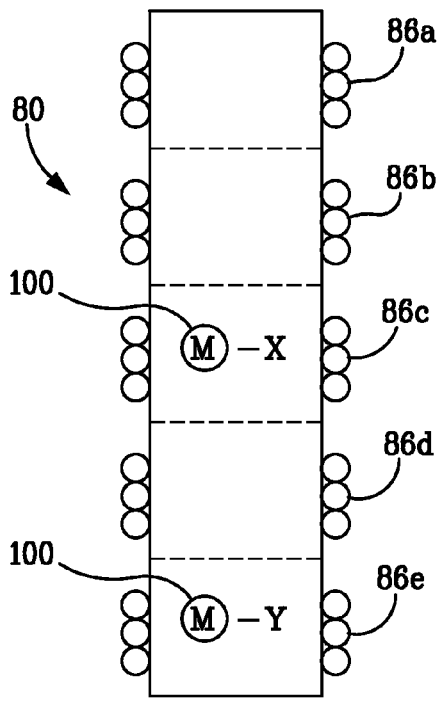
FIG. 12C is a schematic diagram of one application of the apparatus shown in FIG. 10.
Figure 12D:
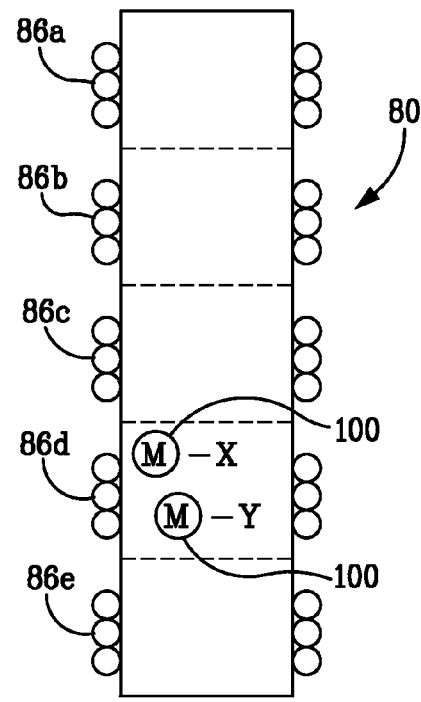
FIG. 12D is a schematic diagram of one application of the apparatus shown in FIG. 10.

The example apparatus 80 can also be used to separate different reactions or different steps of the same reaction. As shown in FIG. 12C, magnetically susceptible components 100 (M reaction X and M reaction Y) are maintained in different regions of the cavity through the systematic activation of coils 86a, 86b, 86c, 86d, 86e. For example, a user might intend to keep two reactions or phases of a reaction separated for a predetermined amount of time, after which the systematic activation of at least coils 86c and 86e can unite the disparate materials and the associated magnetically susceptible components 100 into the region of the cavity adjacent to coil 86d as shown in FIG. 12D. Alternatively, magnetically susceptible components 100 (M-X) can be split into two portions by deactivating coil 86c and simultaneously activating coils 86b and 86d. Additionally, one can move magnetically susceptible particles 100 through different phases (and different reaction conditions) of a single reaction through the systematic activation of the coils 86a, 86b, 86c, 86d, 86e. As one of skill in the art will readily appreciate, the examples described with reference to FIGS. 12A, 12B, 12C and 12D are illustrative in nature only, and any number of permutations of coil activations could be readily implemented to cause any number of desirable motions of the magnetically susceptible components within the cavity.

In one variation of the example apparatus 80, the apparatus can be configured for small-scale reactions using two or more printed circuit boards, each defining a cavity therein, and arranged in a manner such that a central axis of each of the cavities is substantially aligned or collinear. Each of the printed circuit boards can further include a coil such as that described herein, or any other suitable conductive medium imprinted thereon or etched therein in any suitable geometry such as a spiral for generating a magnetic field substantially parallel to the central axis in response to an electrical input. Each printed circuit board can have its own independent electrical source and/or controller connected to the coil for selectively generating the desired magnetic field in the desired direction. Alternatively, each printed circuit board can be connected to one or more external electrical sources and/or controllers for selectively generating the desired magnetic field in the desired direction. In one implementation of this variation of the example apparatus 80, the cavity disposed in the printed circuit boards can be between one micrometer and two centimeters in diameter, or any other suitable diameter configured for receiving a reaction vessel of the type known in the art.

Figure 7:
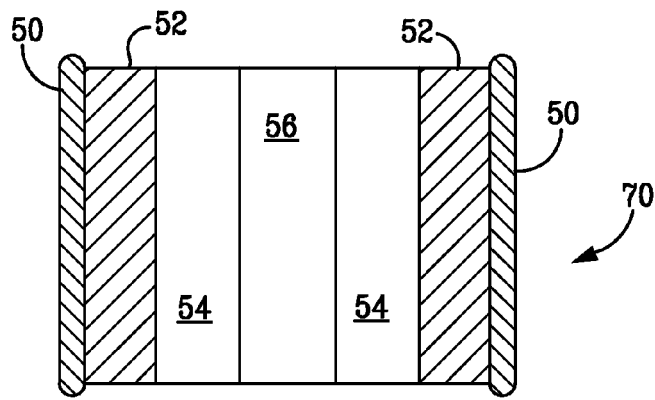
FIG. 7 is a cross-sectional view of an apparatus for mixing, separating or localizing a magnetically susceptible particle with another substance in accordance with another example embodiment of the present invention.

Any of the example apparatuses described herein can include a temperature control means, which as noted above, can be implemented in any number of suitable fashions on either the container, cavity, or any of the aforementioned wiring, coils or segments of wiring for generating electromagnetic fields. FIGS. 7, 8A, 8B, 9A and 9B are illustrative of example apparatuses 70 that employ different types of temperature control means as described herein. FIG. 7 is a cross-sectional view of an example apparatus 70 that includes an electrical layer 50, which can be any of the various configurations of wiring segments, coils and the like described herein. The example apparatus 70 further includes an insulating layer 52 disposed between the electrical layer 50 and a reaction area 54, which can include for example a cylindrical cavity within which a reaction vessel can be disposed. The example apparatus 70 can also include a temperature control means 56, disposed adjacent to the reaction area 54 and distally from the electrical layer 50. The temperature control means 56 can include for example a cavity or container within which a temperature control material or liquid can be disposed for draining heat from or adding heat to the reaction area 54 and maintaining an appropriate reaction temperature.

Figure 8A:
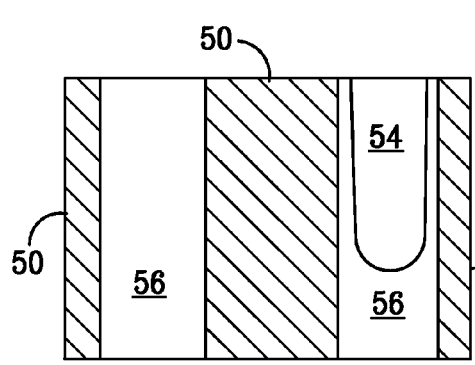
FIG. 8A is a cross-sectional view an apparatus for mixing, separating or localizing a magnetically susceptible particle with another substance in accordance with another example embodiment of the present invention.
Figure 8B:
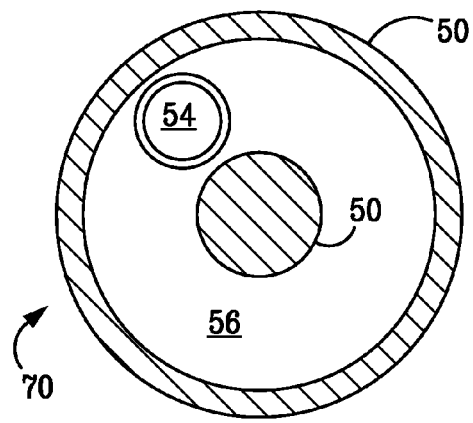
FIG. 8B is a cross-sectional view an apparatus for mixing, separating or localizing a magnetically susceptible particle with another substance in accordance with another example embodiment of the present invention.

Another configuration of the example apparatus 70 is shown in FIGS. 8A and 8B. As shown therein, the example apparatus 70 includes an electrical layer 50 that can include for example a permanent or electromagnet formed as a ring or cylinder bounding a temperature control means 56 as well as a cylinder disposed in a middle portion of the temperature control means 56. The electrical layer 50 can be configured as any variation or combination of the several wiring segments, coils and the like described herein. A reaction area 54 is disposed within the temperature control means 56. The reaction area 54 can include for example a container or cavity for receiving a reaction vessel or for receiving the intended reaction materials. As in the prior example, the temperature control means 56 can include a cavity or container within which a temperature control material or liquid can be disposed for draining heat from the reaction area 54 and maintaining an appropriate reaction temperature.

Figure 9A:
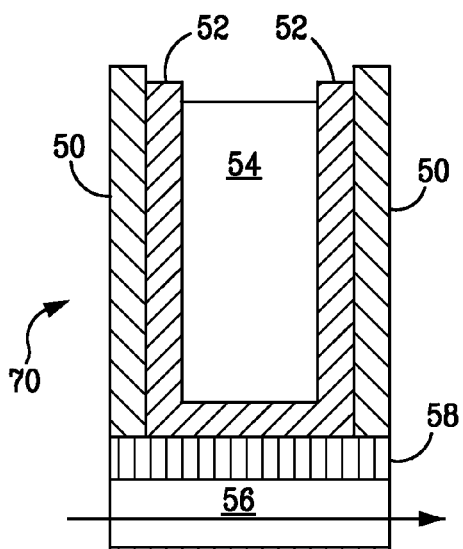
FIG. 9A is a cross-sectional view an apparatus for mixing, separating or localizing a magnetically susceptible particle with another substance in accordance with another example embodiment of the present invention.
Figure 9B:
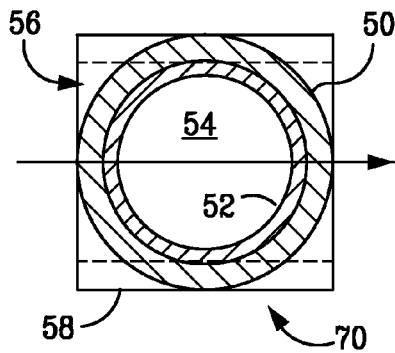
FIG. 9B is another cross-sectional view the apparatus of FIG. 9A.

Another configuration of the example apparatus 70 is shown in FIGS. 9A and 9B. As shown therein, the example apparatus 70 includes an electrical layer 50 that can be configured as any variation or combination of the several wiring segments, coils and the like described herein. An insulating layer 52 can be disposed between the electrical layer and a reaction area 54. As in prior examples, the reaction area 54 can include a container or cavity for receiving a reaction vessel or for receiving the intended reaction materials. The example embodiment 70 shown in FIGS. 9A and 9B can further include a base portion 58 defining a temperature control means 56 therein. The temperature control means 56 can include a cavity, tube or container within which a temperature control material or liquid can passed in the direction of the arrow, thereby functioning as a heat exchanging material or fluid. As in the prior examples, the temperature control means 56 functions to drain excessive heat from the reaction area 54 and maintain an appropriate reaction temperature.

The present invention further includes a system for determining a mass change of a magnetically susceptible polymer component in a reaction. The example system can include an apparatus for mixing, separating or localizing a magnetically susceptible polymer component such as for example any of the example apparatuses and variations thereof described herein, or any other suitable apparatus for mixing, separating or localizing magnetically susceptible components. In particular, the apparatus can include a reaction vessel within which the magnetically susceptible polymer component is mixable with another material and means for generating a magnetic field within the reaction vessel. The means for generating a magnetic field can include one or more electromagnetic elements disposed externally to the reaction vessel and an electrical source adapted to selectively provide electrical current to the one or more electromagnetic elements. The example system can also include a small field coil disposed adjacent to the apparatus. The small field coil can be adapted to detect a mass change in the magnetically susceptible polymer component in response to a change in the inductance of the small field coil.

As a reaction is taking place within the reaction vessel, the functionality of some or all of the magnetically susceptible polymer components can be changed, thus potentially changing the mass of the magnetically susceptible polymer components. Changes in the magnetic field(s) induced by the magnetically susceptible polymer components will cause changes in the impedance of the small field coil, which can be measured in terms of either frequency or current within the small field coil. In order to achieve a consistent and clear understanding of the mass change of the magnetically susceptible polymer components, the system can incorporate additional small field coils as necessary, from which an average impedance and mass change can be determined. Alternatively, the small field coil can be one of the one or more electromagnetic elements that is systematically switched from a current driver to an impedance-measuring element.

To that end, the system can also include a controller connected to the means for generating a magnetic field and the small field coil. The controller can be adapted to control one or more of a plurality of current parameters relating to the magnetic field and further adapted to determine an inductance in the small field coil. As noted above, the current parameters can include current magnitude, a current frequency, a current timing, and a current direction. The controller can be any suitable processor, microprocessor, computer, ASIC, integrated circuit, or device that is adapted to produce a predetermined output in response to a set of machine-readable or manual instructions. The controller can be integrated within the electrical source or operated as a stand-along modular component of the example system.

During the reaction, the relatively large magnetic field employed by the means for generating a magnetic field can obscure any impedance changes in the small field coil. As such, in one suitable mode of operation, the controller of the example system can be further adapted to activate and deactivate the means for generating a magnetic field according to a predetermined duty cycle in order to determine the inductance in the small field coil. The predetermined duty cycle can be between seventy-five percent and ninety-five percent activated and between twenty-five percent and five percent deactivated. For example, the controller can control the means for generating a magnetic field to generate the magnetic field for ninety percent of any given time interval, and then deactivate the means for generating in order to power and operate the small field coil and receive any impedance measurements there from.

Any of the apparatuses and/or systems of the present invention can be readily employed for both macro- and micro-scale reactions, ranging from large scale or batch mixtures for use in the chemical industry as well as micro-scale "lab on a chip" formulations conventionally found in the medical research and pharmaceutical industries. Additionally, any of the apparatuses and/or systems of the present invention can be used for separating magnetic materials from non-magnetic materials, from separating stronger magnetic materials from weaker magnetic materials, and/or isolating or localizing magnetic materials from non-magnetic materials or stronger magnetic materials from weaker magnetic materials.

For purposes of clarity of the principles thereof, the present invention has been described with reference to its example embodiments so as to enable any person skilled in the art to make or use the present invention. However, various modifications to these embodiments will be readily apparent to those skilled in the art including variations relating to the reaction scale, and the generic principles defined herein may be applied to other embodiments without departing from the spirit or scope of the invention as set forth in the following claims.

What is claimed is:

1. An apparatus for manipulating a magnetically susceptible component comprising:
   a cavity for manipulating the magnetically susceptible component with an additional substance, the cavity defining a central axis;
   a first coil disposed circumferentially about the cavity in a first position about the central axis;
   a second coil disposed circumferentially about the cavity in a second position about the central axis;
   a reaction vessel disposed within the cavity;
   a first electrical source connected to the first coil such that in response to a first electrical current passing from the electrical source through the first coil, the first electrical current generates a first individually addressable magnetic field substantially parallel to the central axis; and
   a second electrical source connected to the second coil such that in response to a second electrical current passing from the electrical source through the second coil, the second electrical current generates a second individually addressable magnetic field substantially parallel to the central axis; wherein
   the first and second magnetic fields define distinct, fluidly connected, reaction volumes within the reaction vessel.

2. The apparatus of claim 1, wherein the cavity defines a substantially cylindrical volume.

3. The apparatus of claim 1, wherein liquid is forcible through the reaction vessel under pressure.

4. The apparatus of claim 3, wherein two or more reaction vessels are linked in series or parallel to allow liquid to flow between the two or more reaction vessels.

5. The apparatus of 3, further comprising a faucet attached to reaction vessel to control the flow of liquid.

6. The apparatus of claim 1, wherein the cavity defines a substantially toroidal volume.

7. The apparatus of claim 6, further comprising a pump connected to the cavity, the pump adapted to cause a material to flow within the cavity.

8. The apparatus of claim 7, further comprising one or more valves connected to the cavity and adapted to selectively isolate the material from the magnetically susceptible components.

9. The apparatus of claim 1, further comprising a temperature control mechanism connected to one of the cavity, the first coil or the second coil.

10. The apparatus of claim 1, wherein the first and second electrical sources are integrated into a third, unitary electrical source, and wherein the third electrical source comprises a switch adapted to provide electrical current to at least one of the first and second electrical sources.

11. The apparatus of claim 1, further comprising a controller connected to the first and second electrical sources, the controller adapted to control one or more of a plurality of current parameters of the first and second electrical sources.

12. The apparatus of claim 11, wherein the plurality of current parameters comprises a current magnitude, a current frequency, a current timing, and a current direction.

13. The apparatus of claim 11, wherein the controller is further adapted to control the first and second electrical sources to provide electrical current to the first and second coils in a predetermined pattern in order to optimize the manipulation of the magnetically susceptible components within the apparatus.

14. The apparatus of claim 13, wherein the predetermined pattern comprises one of providing electrical current substantially simultaneously or providing current substantially sequentially.

15. The apparatus of claim 1 wherein the first and second electrical currents differ such that the first and second magnetic fields have detectably different properties.

16. The apparatus of claim 15 wherein the first and second electrical currents differ in their magnitude, frequency, timing, direction, or a combination of two or more of these.

17. The apparatus of claim 15 wherein the detectably different properties of the first and second magnetic fields are the magnitude, frequency, timing, direction, or a combination of two or more of these.

18. The apparatus of claim 1 wherein each magnetic field is defined by an individual coil.

19. The apparatus of claim 1 wherein the reaction volumes have different physical conditions determined by the magnetic field defining the reaction volumes.

20. The apparatus of claim 19 wherein magnetically susceptible components within a first reaction volume behave differently from magnetically susceptible particles in a second reaction volume based on the physical properties within the reaction volumes.

21. The apparatus of claim 20 wherein the behavior is direction of movement.

* * * * *